(12) United States Patent
Cho et al.

(10) Patent No.: US 7,890,162 B2
(45) Date of Patent: Feb. 15, 2011

(54) METHOD AND APPARATUS FOR SENSING IMPROVEMENT USING PRESSURE DATA

(75) Inventors: Yong K. Cho, Maple Grove, MN (US);
Teresa A. Whitman, Dayton, MN (US);
Mark L. Brown, North Oaks, MN (US);
Scott W. Davie, St. Paul, MN (US);
Karen J. Kleckner, New Brighton, MN (US); Charles R. Gordon, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 569 days.

(21) Appl. No.: 11/741,942

(22) Filed: Apr. 30, 2007

(65) Prior Publication Data
US 2008/0269627 A1 Oct. 30, 2008

(51) Int. Cl.
*A61B 5/0452* (2006.01)

(52) U.S. Cl. .................................................. 600/521

(58) Field of Classification Search ............ 607/6, 607/9, 14, 17, 18, 23, 24; 600/521
See application file for complete search history.

(56) References Cited

U.S. PATENT DOCUMENTS

| 3,614,954 | A | | 10/1971 | Mirowski et al. | |
|---|---|---|---|---|---|
| 4,291,699 | A | | 9/1981 | Geddes et al. | |
| 5,702,427 | A | | 12/1997 | Ecker et al. | |
| 6,882,882 | B2 | * | 4/2005 | Struble et al. | 607/9 |
| 6,915,157 | B2 | | 7/2005 | Bennett et al. | |
| 6,934,586 | B2 | * | 8/2005 | Struble et al. | 607/23 |
| 6,959,214 | B2 | * | 10/2005 | Pape et al. | 607/17 |
| 7,096,064 | B2 | * | 8/2006 | Deno et al. | 607/9 |
| 7,130,684 | B2 | * | 10/2006 | Mulligan et al. | 607/9 |
| 2003/0074029 | A1 | * | 4/2003 | Deno et al. | 607/23 |
| 2003/0100925 | A1 | * | 5/2003 | Pape et al. | 607/17 |
| 2003/0199934 | A1 | * | 10/2003 | Struble et al. | 607/17 |
| 2003/0199936 | A1 | * | 10/2003 | Struble et al. | 607/25 |
| 2004/0049235 | A1 | * | 3/2004 | Deno et al. | 607/9 |
| 2005/0070968 | A1 | | 3/2005 | Bergelson et al. | |
| 2005/0080460 | A1 | * | 4/2005 | Wang et al. | 607/17 |
| 2006/0079942 | A1 | * | 4/2006 | Deno et al. | 607/17 |
| 2006/0122651 | A1 | * | 6/2006 | Whitman | 607/14 |
| 2006/0235478 | A1 | * | 10/2006 | Van Gelder et al. | 607/9 |
| 2007/0255151 | A1 | * | 11/2007 | Struble et al. | 600/513 |
| 2007/0255327 | A1 | * | 11/2007 | Cho et al. | 607/18 |

* cited by examiner

*Primary Examiner*—Niketa I Patel
*Assistant Examiner*—Hiba El-Kaissi
(74) *Attorney, Agent, or Firm*—Stephen W. Bauer; Reed A. Duthler

(57) ABSTRACT

Method and apparatus for sensing improvement using pressure data. The method and apparatus may be used in an implantable medical device to confirm that an EGM event signifies a true mechanical cardiac activity and not just electrical oversensing. The mechanical activity may be used to create a mechanical marker channel in the implantable medical device.

6 Claims, 10 Drawing Sheets

METHOD AND APPARATUS FOR SENSING IMPROVEMENT USING PRESSURE DATA

BACKGROUND

Implantable medical devices (IMDs), such as cardiac pacemakers and defibrillators, are useful for management of a variety of cardiac conditions such as congestive heart failure, conduction defects and arrhythmias. Since IMDs typically deliver therapies based on sensed electrical cardiac activity, the ability of IMDs to accurately detect and interpret cardiac electrical signals is essential to the delivery of proper therapies.

Implantable medical devices typically sense cardiac electrical activity through electrodes implanted in or around the heart and/or other locations within the patient's body, which produce cardiac electrograms (EGMs). The quality of the data provided by the electrodes affects the ability of the IMD to correctly interpret the cardiac activity. The electrical cardiac signals received by the IMD may be negatively affected by factors such as pathological changes in the heart's intrinsic activity, lead maturation effects such as changes in the positioning of implanted leads, or changes in the conductive properties of the heart muscle in the region surrounding the leads, such as might result from myocardial infarction and fibrotic tissue growth around the lead. In addition, certain non-cardiac signals, such as electromagnetic noise, myopotentials, and the like, must be distinguished by the IMD from true cardiac electrical activity.

The ability of an IMD to sense cardiac signals is typically controllable by means of circuitry for adjusting the sensitivity threshold of the pacemaker's sense amplifier, such that electrical signals resulting from depolarization of the cardiac muscle must exceed this threshold in order for the cardiac event to be recognized. The sense amplifier circuitry of the IMD must be sensitive enough to ensure detection of cardiac signals, which are typically of relatively low magnitude, especially in the case of atrial sensing. However, the sense amplifier must not be so sensitive that certain non-cardiac signals, such as electromagnetic noise, myopotentials, and the like, cause the IMD to erroneously sense a cardiac signal which did not actually occur. For example, in the case of pacemakers, if the sense amplifier circuitry is not sensitive enough (undersensing), the pacemaker could lose synchronization with the natural cardiac rhythm or deliver pacing stimuli at inappropriate times. However, if the sense amplifier circuitry is set too low (oversensing), the pacemaker could erroneously sense a cardiac signal which did not occur. Similarly, defibrillators which are oversensing could detect an arrhythmia and deliver an inappropriate spurious shock. Thus, while sensitivity adjustments help to refine the ability of an IMD to detect electrical signal, undersensing, oversensing and poor signal quality create a risk that the IMD may incorrectly interpret an electrical signal. An improved system or method that provides the appropriate level of sensing is therefore desirable.

BRIEF DESCRIPTION OF THE DRAWINGS

The following drawings are illustrative of particular embodiments of the present invention and therefore do not limit the scope of the invention. The drawings are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

Implantable medical devices (IMDs) may be used to monitor and deliver therapy to a patient's heart. IMDs typically sense a patient's cardiac electrogram, interpret the electrogram to represent a cardiac rhythm, and deliver therapy based on that interpretation. Accurate electrical sensing and data interpretation are therefore essential to the delivery of appropriate therapy such as IMDs. Embodiments of this invention employ intracardiac pressure data for monitoring cardiac activity. Such pressure data may be used alone for patient monitoring or in conjunction with EGM, such as to confirm the accurate interpretation of EGM data. Certain embodiments of the invention may include, or may be adapted for use in, diagnostic monitoring equipment, external medical device systems, and implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

Figure 1:
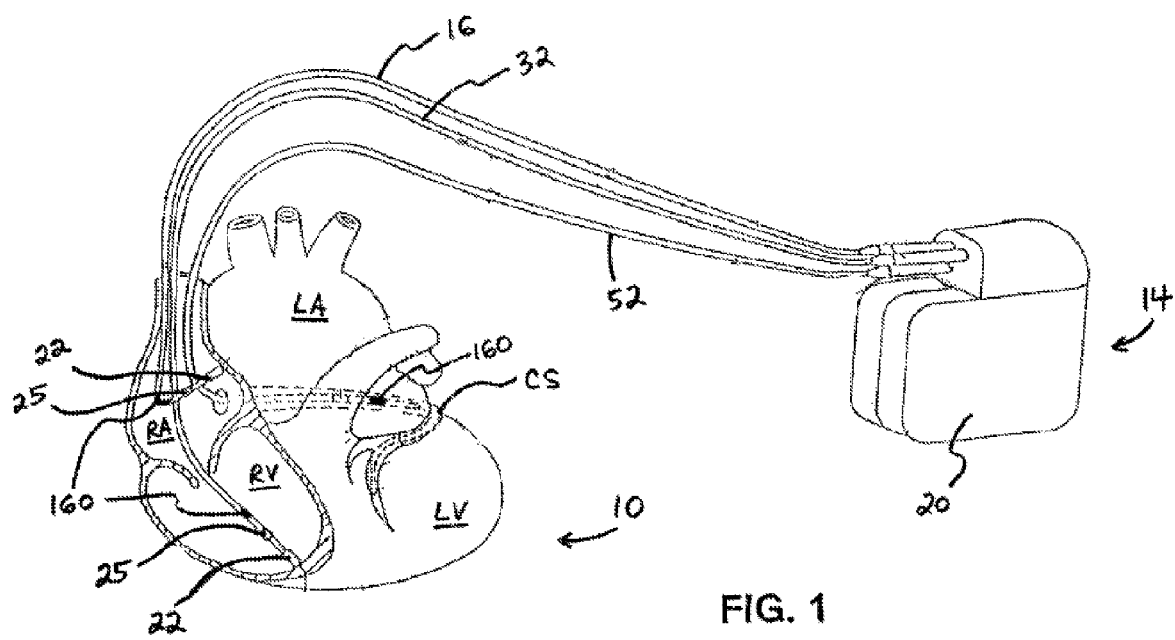
FIG. 1 is a schematic diagram depicting a multi-channel, atrial and bi-ventricular, monitoring/pacing implantable medical device (IMD) in which embodiments of the invention may be implemented.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

In FIG. 1, heart 10 shows the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, as well as incorporating electrodes which are spaced apart which function as impedance sensing leads for deriving volumetric measurements of the patient's torso and expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
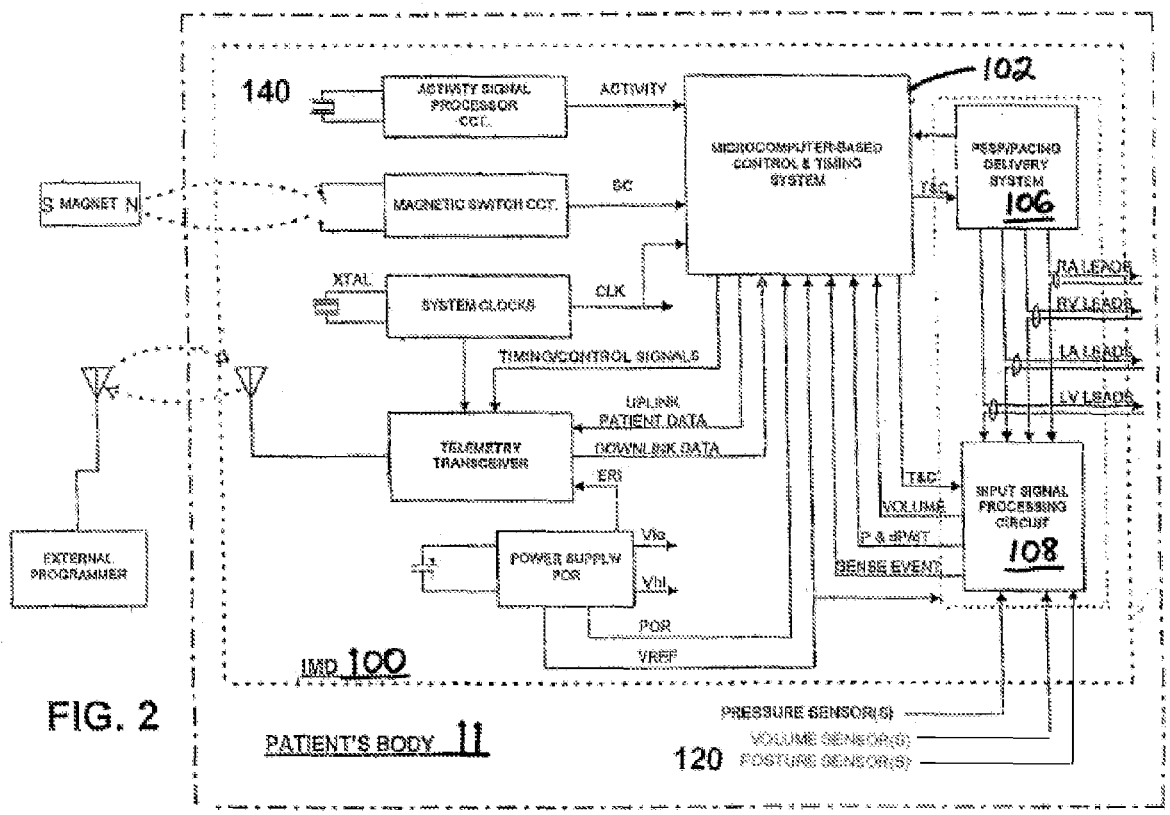
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors.

Figure 3:
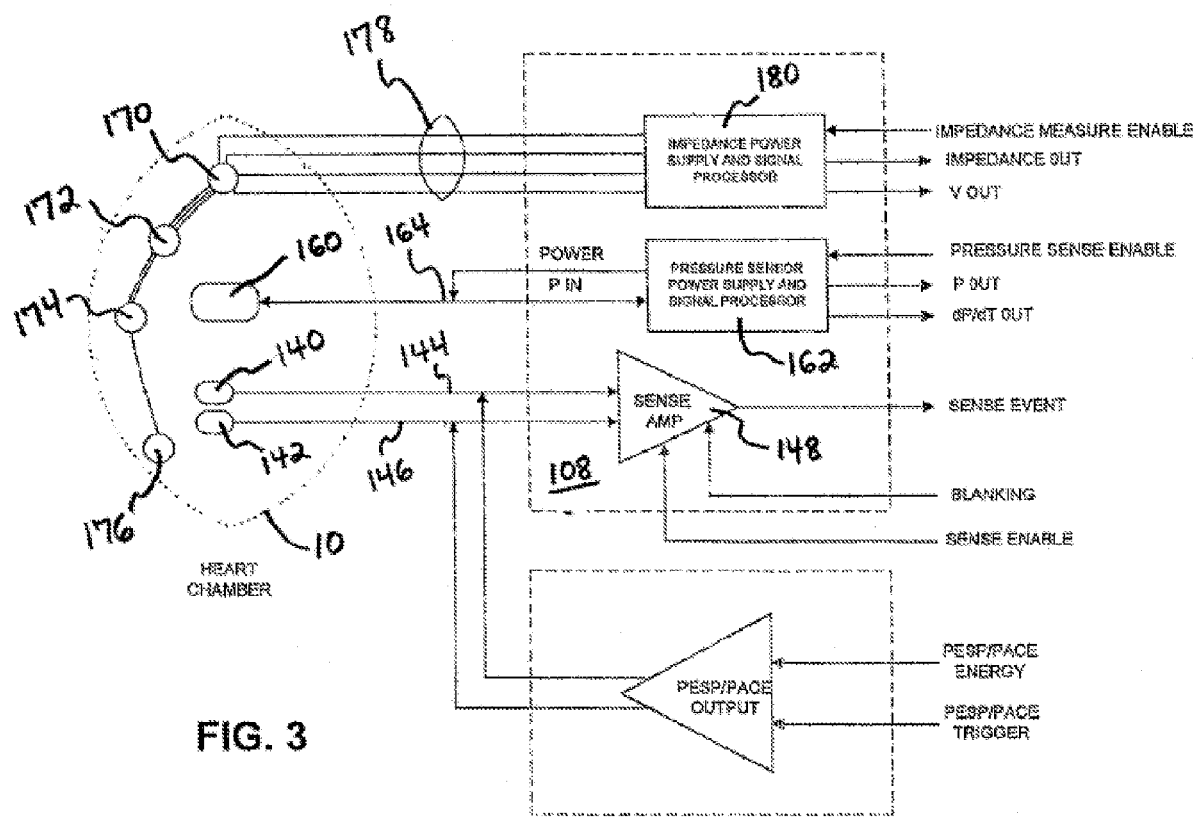
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

Figure 4:
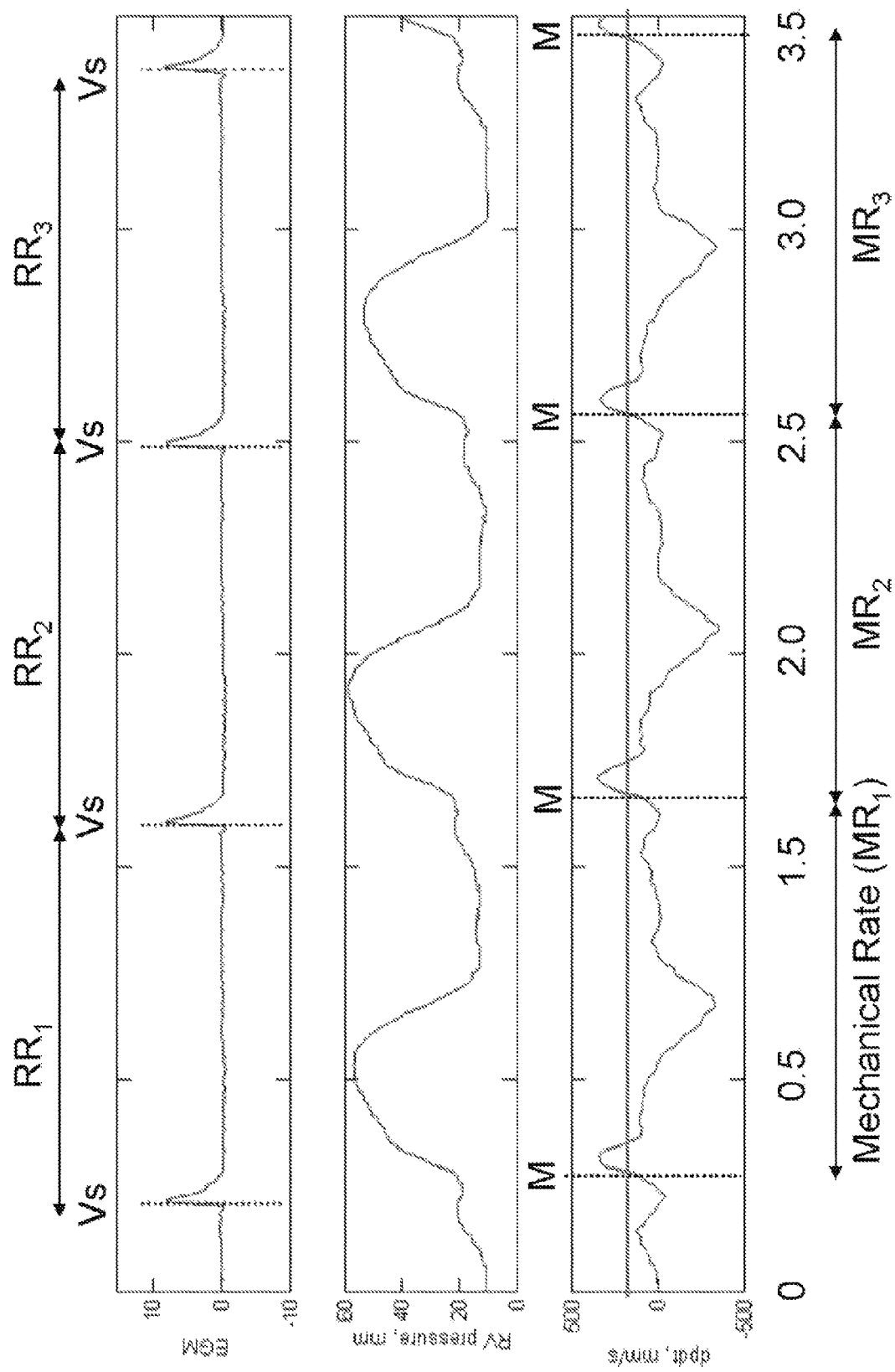
FIG. 4 is simultaneous recording over time of an EGM, right ventricular intracardiac pressure, and right ventricular dP/dt, with a marker channel M set at a threshold right ventricular dP/dt of 100 mmHg/s.

An example of an electrogram 200 is shown in the top row of FIG. 4. The associated right ventricular pressure is shown in the middle row 210, while the change in right ventricular pressure over time, dP/dt 220, is shown in the bottom row and is derived from the pressure data of the middle row. A mechanical impulse can be seen as an increase in pressure and a dP/dt maximum 222 following each electrical signal 202, indicating that the right ventricular electrical sensing is appropriate.

Various measurements may be used to detect the presence of mechanical activity. For example, pressure data may be detected and interpreted as an indication of mechanical activity of the heart. Such pressure data includes, for example, absolute systolic pressure, absolute diastolic pressure and pressures corrected for atmospheric pressure. Other parameters may also be used to indicate mechanical activity. For example, a pressure waveform may be used to derive variables such as dP/dt, pulse pressure, estimated pulmonary arterial pressure, pre-ejection intervals, diastolic time interval and systolic time interval. In embodiments which monitor dP/dt or pulse pressure, no external reference is necessary for the pressure measurement. In addition, such embodiments may be less affected by sources of pressure changes such as postural changes. Other methods of measuring mechanical activity of the heart which may be used include, without limitation, impedance measurements, accelerometers, and tensiometers.

The IMDs of various embodiments of the invention may store and/or transmit sensed data using marker channels. Such marker channels abstract information from readings such as EGMs into a more simplified form, a marker channel, which marks the presence of physiological events and the relative time of the event. For example, marker channels may mark the presence of sensed and stimulated atrial and ventricular depolarizations. In some embodiments of the invention, pressure data and/or other data indicative of mechanical activity may be stored and/or transmitted by a marker channel indicative of mechanical activity. This mechanical marker channel or mechanical sensed channel (M channel) marks the occurrence of a mechanical event at a particular time. In some embodiments, the M channel may be a pressure-based marker channel. The IMD may monitor pressure values such as right ventricular pressure or right ventricular dP/dt to determine that a mechanical event has occurred. The occurrence of the mechanical event may be noted, stored and/or transmitted using the M channel. Thus mechanical activity may be continuously monitored while simplifying the data such that battery usage, storage memory and data transmission are minimized.

The occurrence of a mechanical event may be determined by a measurement of mechanical activity exceeding a threshold value 230. For example, the IMD may measure RV pressure or RV dP/dt. When the RV absolute pressure or RV dP/dt exceeds the threshold 230, a mechanical event is considered to have occurred and is marked on the M channel. For example, in some embodiments, the IMD continuously monitors RV pressure. Each time the RV dP/dt exceeds a threshold 230, such as 100 mmHg/s, it is marked on the M channel as a mechanical event 240 occurring at that moment. An example of the use of dP/dt 220 to identify mechanical activity 240 for a marker channel is shown in FIG. 4. In this example, when dP/dt 220 crosses a threshold value 230 of 100 mmHg/s, the presence of mechanical activity 240 is marked on the M channel.

In some embodiments, the threshold value 220 for detecting a mechanical event may be set relatively low such that all organized cardiac contractions are interpreted and marked as mechanical events. The threshold 230 may be preset or may be programmable. For example, in some embodiments which monitor RV dP/dt 220, the threshold 230 for the maximum value may be anywhere from about 75 to about 125 mmHg/s. In some embodiments, the maximum positive RV dP/dt threshold 230 is set at about 100 mmHg/s. The RV dP/dt threshold 230 may be set such that both weak and strong contractions are marked as mechanical activity 240. In some embodiments, the strength of the mechanical activity 240 may also be marked, such as by using various mechanical markers to indicate different levels of mechanical activity 240 on a marker channel or on a different channel. For example, the amplitude of mechanical activity information could be translated into markers indicating weak, baseline or strong activity such as $M_w$, $M_b$ and $M_s$. Alternatively, the strength of the mechanical activity 240 may be stored as data by the IMD. The strength of the mechanical activity 240 may be determined, for example, by the value of dP/dt max 222, maximum pressure, or pulse pressure for each detected mechanical event 240.

In some embodiments, electrical activity markers may be stored on their own channel or channels while mechanical data is simultaneously stored on a separate marker channel. In other embodiments, both electrical and mechanical markers may be stored on the same channel. In this way, electrical activity may be cross referenced with mechanical activity. When electrical sensing is appropriate, a mechanical event is expected to follow each electrical event.

Embodiments of the invention may monitor the electrical and mechanical channels for synchrony between the electrical and mechanical events. The presence of an electrical event without a mechanical event may occur in a variety of circumstances such as electrical oversensing of signals other than R-waves, such as rapid electrical rates, closely coupled PVCs that are too rapid to produce a measurable mechanical event, pulseless electrical activity, and electrical/mechanical dissociation. An example of electrogram oversensing of a signal other than an R-wave is T-wave oversensing, which occurs when a T-wave is detected and interpreted by the IMD to be an R-wave. Such T-wave oversensing may occur, for example, during sinus tachycardia. In such a circumstance, if T-wave oversensing is occurring with every T-wave, some electrical events are true R-waves and are associated with a mechanical event. The other electrical events are T-waves which are erroneously interpreted to be R-waves. These T-waves do not correspond to electrical stimulation of the cardiac tissue and therefore have no associated mechanical event. The lack of an associated mechanical event may therefore be used to distinguish true R-waves from oversensed T-waves.

Figure 5:
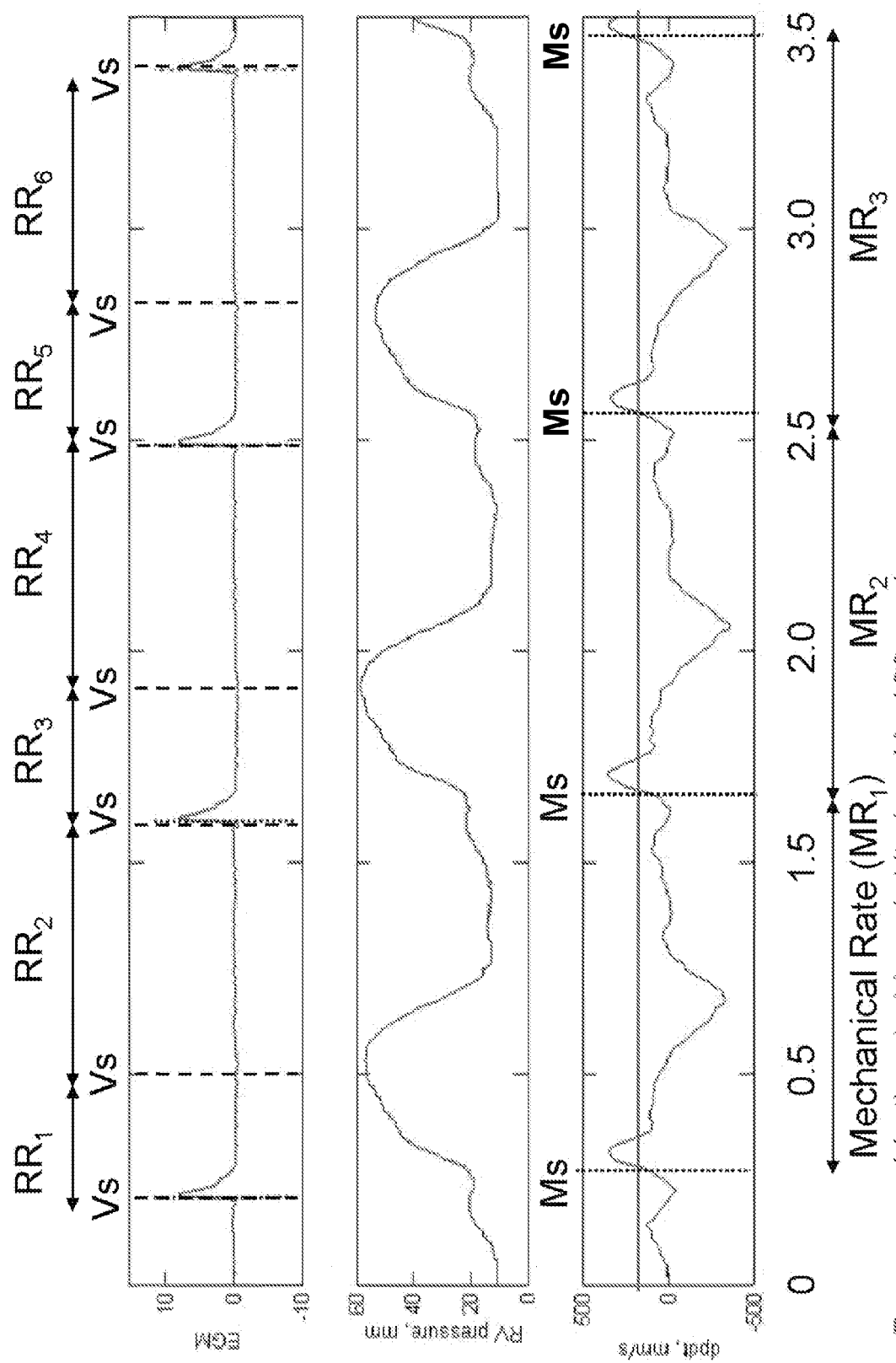
FIG. 5 is a simultaneous reading over time of an EGM, right ventricular intracardiac pressure, and right ventricular dP/dt, simulating T-wave oversensing on the EGM recording.

An example of T-wave oversensing is demonstrated in FIG. 5. In this example, every other detected electrical event 302 on the EG-M 300 is actually a T-wave 304 which is misinterpreted as a ventricular event and recorded on the electrical marker channel as an electrical event 302. However, only electrical activations 302 that elicit measurable ventricular contractions are recorded as mechanical events 340. These true ventricular contractions are detected in this example by the RV dP/dt 320 exceeding a threshold 330 of 100 mmHg/s. The mechanical events 340 are recorded on the M Channel as strong contractions, $M_s$ 350. The IMD uses this data to calculate the mechanical interval (MR) 350 as the time between two successive mechanical events.

Figure 6:
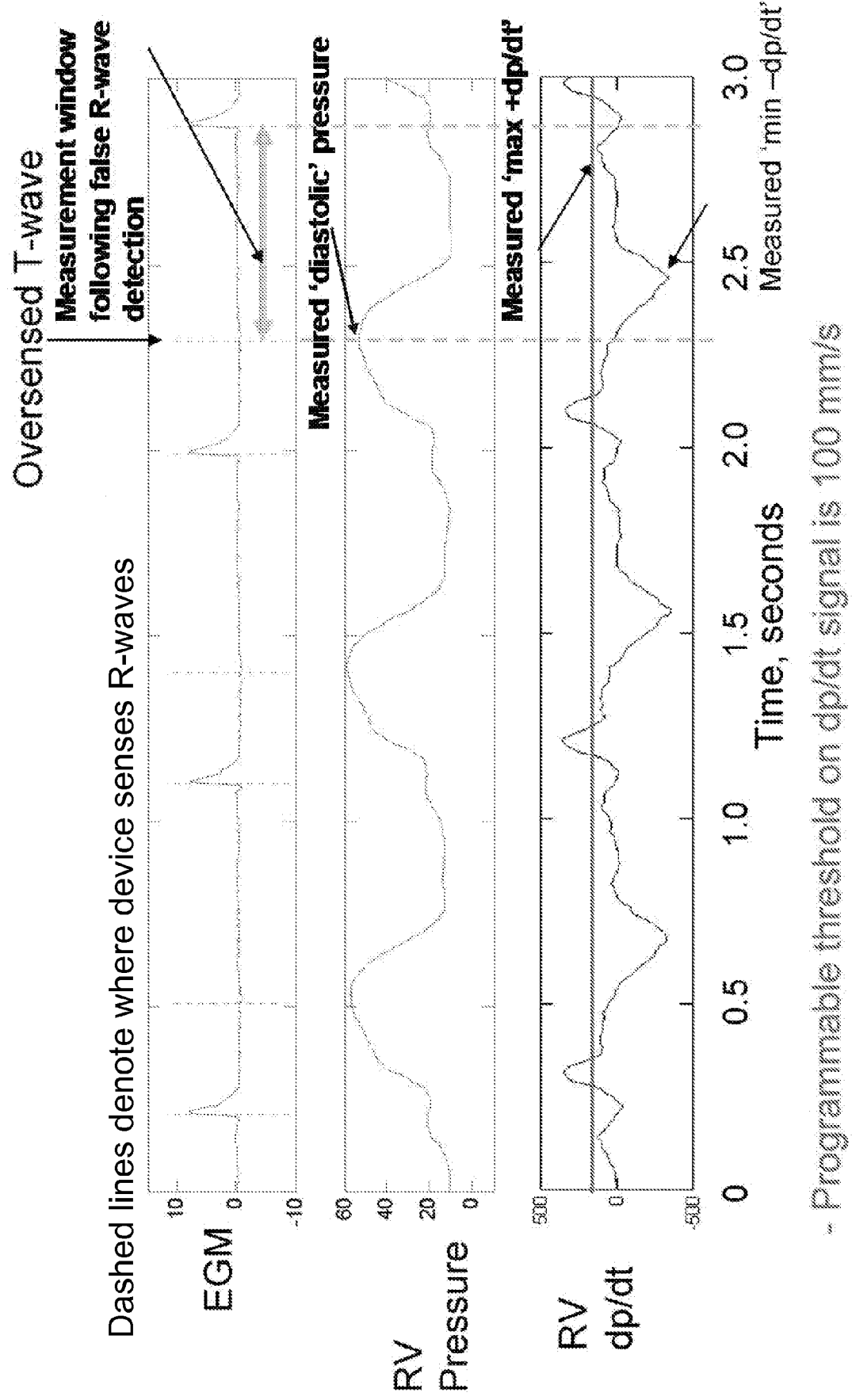
FIG. 6 is a simultaneous reading over time of an EGM, right ventricular pressure, and right ventricular dP/dt, demonstrating an oversensed T-wave followed by a right ventricular dP/dt measurement window.
Figure 8:
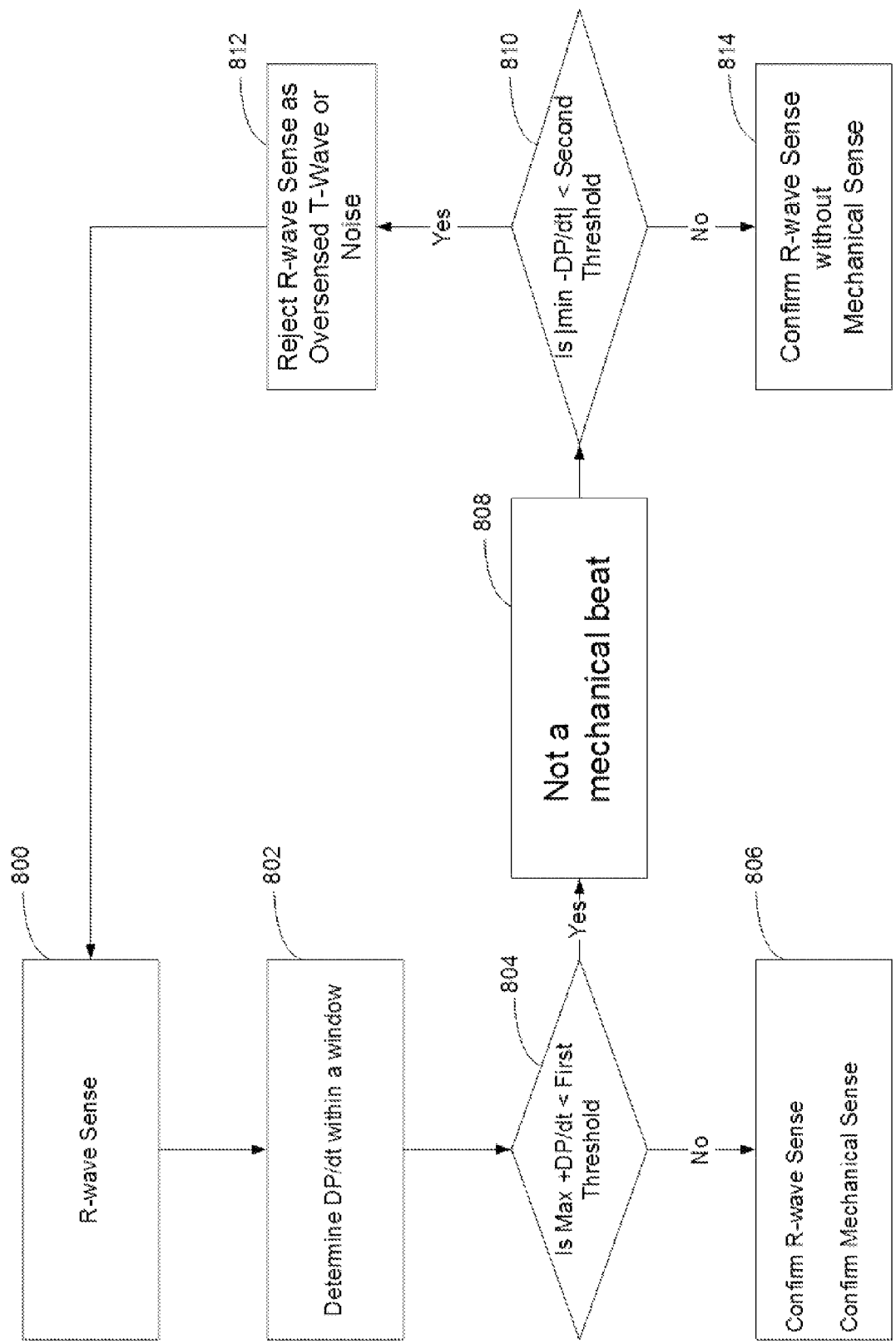
FIG. 8 is a flow chart demonstrating a method of differentiating R-waves, with and without mechanical sensed events, and T-waves using pressure data.

The IMD may use the maximum positive dP/dt 422 and the minimum negative dP/dt 424 to determine whether an electrical event 402 measured on an EG-M 400 represents a true R-wave. An example of this is shown in FIG. 6. RV pressure 400 and RV dP/dt 420 are measured simultaneously with the EG-M 400. According to some embodiments, after detection of an electrical event 402, a window opens for measuring maximum positive and minimum negative dP/dt 422,426. An example of such an embodiment is demonstrated in FIG. 6. The window may be, for example, in the range of about 400 ms to about 500 ms from the electrical event, or until the next electrical detection occurs, whichever occurs first. During this window, the maximum and minimum dP/dt 422, 424 are identified, according to some embodiments. As shown in FIG. 8, the IMD senses an R-wave 800 and determines dP/dt within a window 802. The maximum dP/dt is then compared to a first threshold 804. If the maximum dP/dt exceeds a first threshold and occurs within a window of time following the electrical event, the electrical event is correlated with a mechanical event and the electrical event is identified as a true R-wave 804. However, if the maximum dP/dt does not exceed the first threshold, there is no mechanical beat 808. The absolute value of the minimum dP/dt is then compared to a second threshold 810. If the electrical event is an oversensed T-wave, there will be a negative dP/dt peak within the time window, as shown in FIG. 6. The negative dP/dt peak is referred to as minimum negative dP/dt 424 and indicates the presence of active and passive relaxation of the ventricle after a contraction. Thus, if the absolute value of maximum positive dP/dt 422 is less than a threshold and absolute value of the minimum negative dP/dt 424 is greater than the absolute value of a second threshold, the electrical activity is interpreted to be a T-wave or oversensed noise 404 that is occurring following a true R-wave 812. The absolute value of the second threshold may be, for example, about 150 mmHg/s. The absolute value of the second threshold may optionally be in the range of about 100 mm Hg/s to about 250 mmHg/s. If both the maximum positive dP/dt and the absolute value of the minimum negative dP/dt do not exceed the thresholds, there has been no contraction or relaxation and the initial test is indeterminate 814. Such an electrical event must then be interpreted to be an R-wave without associated mechanical activity such as might occur during rapid rhythms such as ventricular fibrillation, ventricular tachycardia, rapidly conducted supraventricular tachycardias, myopotentials, noise, mechanical alternans or a bigeminal rhythm. The presence of an R-wave sense without a mechanical event has different implications, depending on the sensed heart rate and the sensed mechanical rate. The device may then compare the mechanical heart rate and/or the average mechanical amplitude to the measured electrical event rate to determine whether the measured electrical event rate was accurate.

Figure 7:
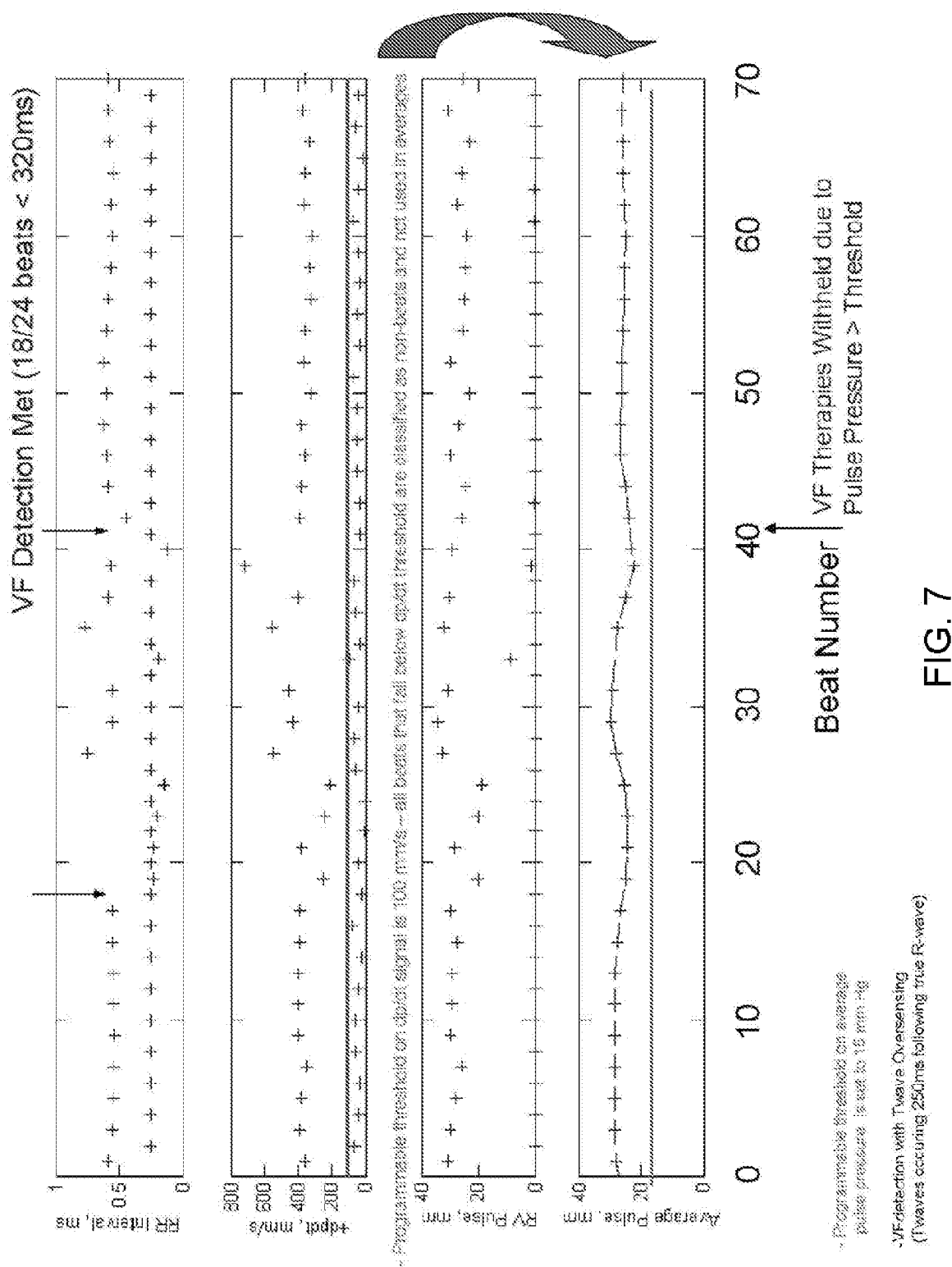
FIG. 7 is a simultaneous reading over time of RR intervals, right ventricular dP/dt, RV pulse pressure, and the average pulse pressure of beats for which the right ventricular dP/dt exceeds a threshold of 100 mmHg/s.

An example of electrical oversensing is demonstrated in FIG. 7. The top row is a plot of the time interval between successive electrical events 506 as detected by an IMD. The IMD interprets each electrical event to be an R-wave, and thus the time interval in the first row is labeled the RR interval. The pressure data in the other rows of this figure can be used to confirm or reject the device's interpretation of the electrical events. The second row of FIG. 7 is a corresponding plot of right ventricular dP/dt 520 and the third row is right ventricular pulse pressure 570. At the beginning of the recording, the top row reveals an alternating pattern of long and short RR intervals 507, 508. The shorter interval 508 is 250 ms in this example and reflects the interval between the R-waves and T-waves (or other noise). Measurement of the corresponding pressure 570 and dP/dt signals 520 for these short RR intervals 506 show the maximum positive dP/dt 522 less than the detection threshold 530 of 100 mm/s and therefore there is no corresponding pulse pressure for the oversensed T-wave. If minimum negative dP/dt does not confirm T-wave or noise oversensing, then the IMD may consider additional information from mechanical rate, interval or amplitude. As shown in FIG. 7, only events having a maximum positive dP/dt 522 greater than a threshold 530 are classified as mechanical events. The mechanical events may then be used to calculate the mechanical rate or mechanical interval and the average amplitude of the mechanical signal 572 (shown as pulse pressure in the example).

Referring again to FIG. 7, the RR interval abruptly decreases to less than 320 ms at beat number 18 500. This rate is fast enough to be detected as ventricular fibrillation by devices which interpret ventricular fibrillation to have occurred after a certain number of fast electrical events, such as 18 electrical events. As shown in the second row of this figure (dP/dt 520), every other electrical beat is not associated with a mechanical event. The average mechanical heart rate is less than 100 beats per minute (mechanical interval of 600 ms) and the average pulse pressure 572 (bottom row) and maximum positive dP/dt 522 are within a normal range. The IMD may consider the heart rate, pulse pressure and maximum positive dP/dt to be normal if they stay within a predetermined range or above or below a predetermined threshold. Measurement of a normal, consistent mechanical rate (e.g., about 50 to about 150 beats per minute) and a strong mechanical amplitude therefore allow the IMD to reject the interpretation of the detected electrical events as representing ventricular fibrillation. By monitoring both electrical events and mechanical events, the IMD is able to confirm that RR intervals 506 associated with a maximum positive dP/dt 522 above a threshold 530 are true R-waves. The IMD is able to further detect oversensing of a T-wave or noise by confirming that an electrical event is associated with a maximum negative dP/dt, the absolute value of which is above a second threshold while a maximum positive dP/dt is not greater than a first threshold. The IMD is thus able to confirm or reject the interpretation of an electrical signal by using mechanical data including measured RR intervals, mechanical intervals, and mechanical amplitudes.

By using mechanical rate and amplitude, the IMD is able to detect the presence of T-wave oversensing and to react appropriately. With electrical monitoring alone and no pressure monitoring, the presence of T-wave oversensing with short RR intervals 506, as shown in FIG. 7, could be interpreted by the IMD as ventricular tachycardia such that an electrical shock could be inappropriately delivered for defibrillation once the detection threshold is reached. However, by using pressure data, the IMD is able to interpret the data to represent T-wave oversensing with adequate mechanical activity, and thus delivery of a spurious shock is avoided.

In addition to detecting a mechanical event associated with each electrical event, the IMD may assess the quality and rate of the mechanical events in order to confirm the accuracy of the interpretation of the electrical signal and to determine the appropriate response. For example, as shown in the bottom row of FIG. 7, the pressure for each mechanical event having a maximum positive dP/dt above a threshold was used to calculate an average pulse pressure 272. In this example, the average pulse pressure 272 is the average of the previous 4 pressure measurements, including only those measurements determined to correlate to true electrical events. The average may include, for example, from 3 to 8 pressure measurements. Thresholds or ranges of the magnitude of the mechanical events individually, or of the averages of more than one mechanical event, may be used to determine the quality of a mechanical event, such as whether the mechanical amplitude is strong, weak, adequate or inadequate. The quality of the mechanical event may then be marked on a marker channel.

Figure 9:
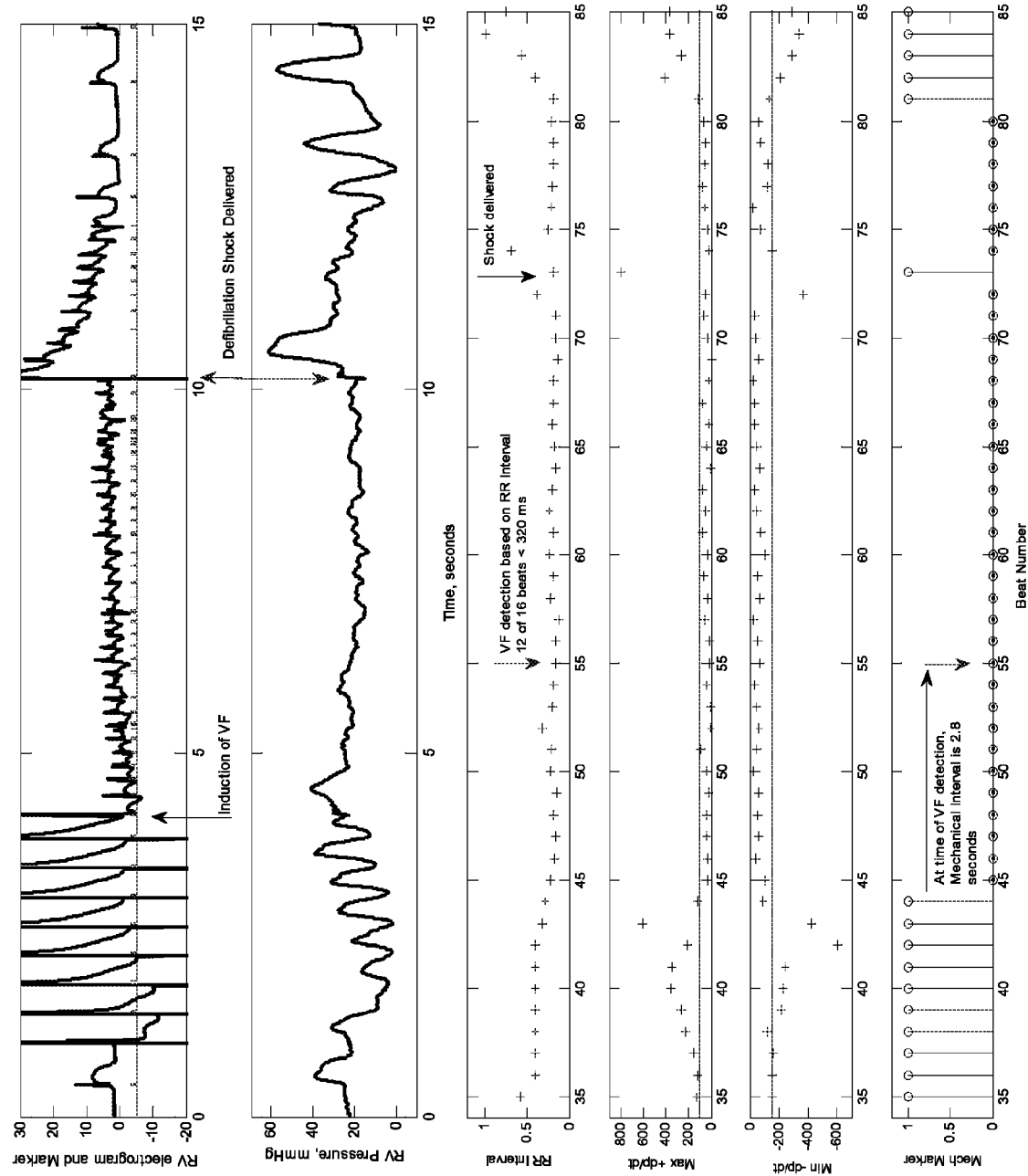
FIG. 9 is a simultaneous reading over time of mechanical and electrical data during an episode of induced ventricular fibrillation.

The use of a mechanical activity average may be particularly useful in tachyarrhythmias, where the average heart rate is high and the average dP/dt and pulse pressure may decrease. In cases where the IMD detected electrogram rate and/or morphology indicates a tachycardia, the IMD could require a threshold for mechanical rate (e.g. 60 beats/minute) and/or mechanical event amplitude (e.g. 70% of baseline pressures at 60-80 beats/minute) that would ensure that the patient could maintain adequate blood pressure to maintain consciousness during the rapid rhythm. Rapid heart rhythms that are not associated with syncope (loss of consciousness) or pre-syncopal symptoms are considered to be hemodynamically stable rhythms. For cases of fast, irregular rhythms such as atrial fibrillation, ventricular tachycardia or ventricular fibrillation, there may be true electrical activations that do not produce a mechanical event as detected by the maximum positive dP/dt threshold. For example, hemodynamically stable atrial fibrillation may produce irregular mechanical events, both in rate and amplitude. In such a case, the mechanical rate threshold and/or the average mechanical amplitude may be used by the IMD to determine whether a rhythm is hemodynamically stable. As shown in the example of FIG. 7, the mechanical rate is approximately 100 bpm and the average pulse pressure 272 remains above the pressure threshold 274 indicating that the mechanical activity of the heart is adequate and no intervention is required. The example of FIG. 9 shows an induced episode of ventricular fibrillation. The top row shows the recorded electrogram 600 with each vertical dashed bar denoting a sensed R-wave 602, as in an electrical ventricular marker channel. The second row shows the recorded right ventricular pressure waveform 610. The third row shows the RR interval 606 that is calculated by the device as the time between successive electrical ventricular markers 602. The fourth and fifth rows show the beat-by-beat measurement of maximum positive dP/dt 622 and minimum negative dP/dt 624. The sixth row is the mechanical marker 622 which marks a mechanical event 640 when the maximum positive dP/dt 622 exceeds a threshold 630 of 100 mm/s. In this example, the IMD detected rapid RR intervals 606 by monitoring the electrogram 600 and identified the rhythm as ventricular fibrillation. The mechanical activity confirms that this identification is correct since no mechanical events 640 were recorded in 2.8 seconds, equaling a rate of 21 beats per minute, which is much slower than the minimum threshold of mechanical beat rate of 60 beats per minute for ventricular fibrillation detection.

In addition to discriminating true R-waves from T-waves, the presence of mechanical pulse alternans may be identified by some embodiments of the invention. For example, the IMD may detect a mechanical event associated with each electrical event. However, the mechanical events may alternate between strong and weak contractions, which may be evident from the measurement of mechanical activity. For example, mechanical events identified by maximum positive RV dP/dt greater than a threshold may occur with each electrical event. However, the mechanical events may alternate between a large maximum positive dP/dt or pulse pressure and a small maximum dP/dt or pulse pressure. This alternating mechanical response would have the same mechanical heart rate as electrical heart rate, but would have an alternating mechanical amplitude. When mechanical pulse alternans is detected, the machine may record the incident and/or may send notification to the patient and/or physician.

In some circumstances, there may be electrical signals that are not associated with any measurable contraction 808, such as in FIG. 8. A combination of mechanical rate and mechanical amplitude can be used by the IMD to determine that no therapy is warranted, such as in FIG. 7. The IMD may record the incident and may send notification to the patient and/or physician.

In some circumstances, the IMD according to embodiments of this invention, may detect a mechanical signal with no associated electrical signal. Such a phenomenon may occur due to undersensing, loss of capture, or dislodgement of a lead. In such circumstances, sensitivity adjustment or movement or replacement of the lead may be necessary.

In some embodiments, the electrical signal and the mechanical signal may be continuously monitored, independent of each other and without the use of windowing. Thus, rather than opening a mechanical detection window after detection of an electrical event, the IMD may continuously monitor mechanical activity, uncoupled from electrical activity. However, time windows may be used for determining whether an electrical and a mechanical signal are correlated. For example, a time interval corresponding to the pre-ejection interval, PEI, may be used as the window during which an electrical event and a mechanical event must occur in order to be correlated. Such windows may be monitored with each beat, though the timing of the window may vary depending upon heart rate and whether the beat is paced, sinus or ectopic. In some embodiments, the window may be, for example, about 400 ms or about 500 ms. In some embodiments, the window may be from a first electrical event to a subsequent electrical event, such that a mechanical event occurring between the first electrical event and the subsequent electrical events is correlated with the first electrical event. Such windows may be useful at elevated rates, such as heart rates of less than about 400 ms between electrical events. The correlation between an electrical and mechanical event may be evaluated by the IMD by a comparison of the electrical events marked on the electrical channel and the mechanical events marked on the M channel.

Figure 10:
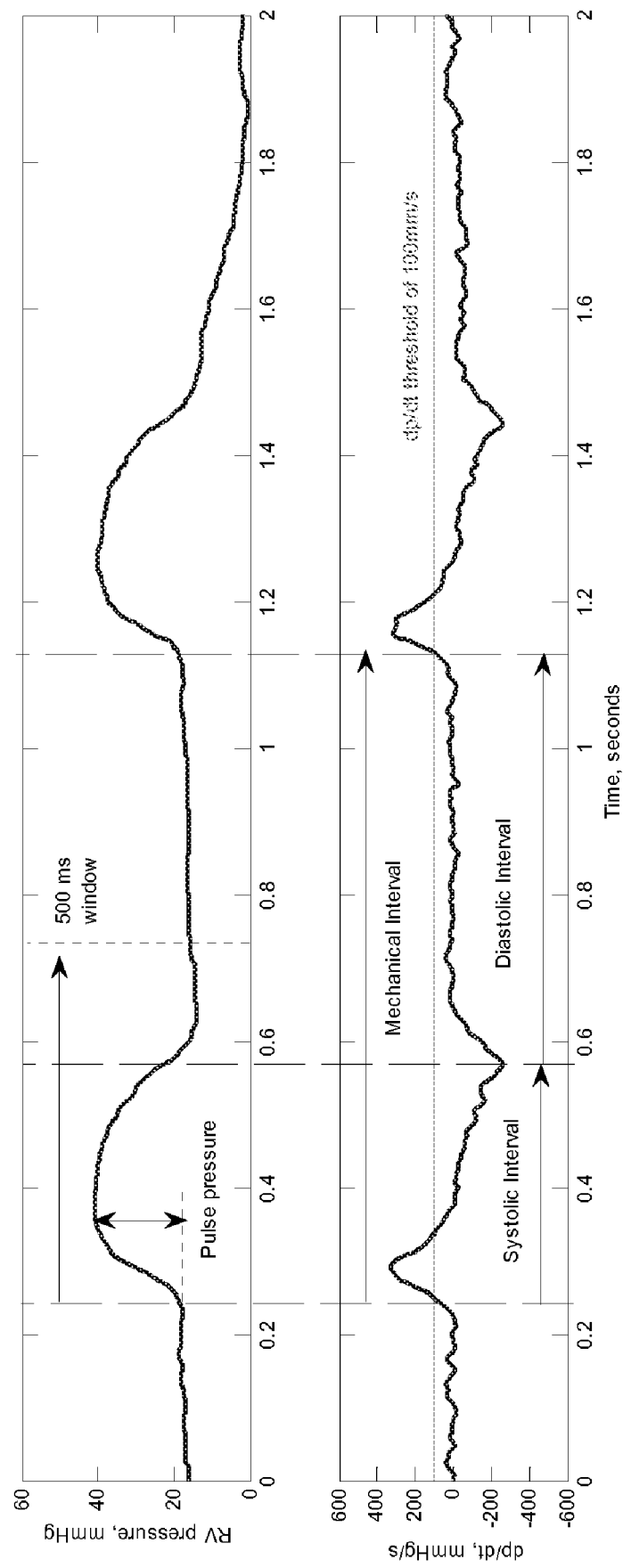
FIG. 10 is a simultaneous reading over time of right ventricular pressure and right ventricular dP/dt.

In some embodiments, mechanical activity may be detected using more than one variable related to mechanical activity. In these embodiments, the use of more than one measurements of mechanical activity may provide confirmation of the sensed mechanical event. For example, in some embodiments mechanical activity may be continuously sensed using right ventricular pressure 710 to derive dP/dt 720. When dP/dt 710 exceeds a threshold value 730, a mechanical contraction is noted by the IMD. The IMD may also monitor pulse pressure 770. In some embodiments, a window 780 for detection of the second measurement of mechanical activity may be gated off of the first measurement of mechanical activity. For example, a window 780 for measurement of pulse pressure 770 may open when dP/dt 720 crosses the mechanical activity threshold 730. In this way, pulse pressure 770 may be used to confirm that the mechanical event sensed using dP/dt 720 was a true mechanical event and not an artifact. Thus the one or more additional variables related to mechanical activity may serve as cross checks to ensure accurate detection and interpretation. An example of this is shown in FIG. 10.

In addition to, or as an alternative to, detecting mechanical activity in the ventricles, some embodiments of the inventions may detect mechanical activity in an atrium. For example, the IMD may detect pulse pressure or dP/dt in the right atrium. Such embodiments may also be useful for detection of far field R-waves, which may be associated with an over estimate of the atrial rate. As with the detection of T-wave oversensing, the IMD may detect the far field R-wave as an electrical event but may determine that it is a far field R-wave, rather than a true R-wave, by the lack of correlation between the far field R-wave and a mechanical event.

In some embodiments, the mechanical event data may be used by the IMD to determine the patient's rhythm, rather than an EGM. Thus, in addition to confirming that an electrical event detected by an EGM represents a ventricular contraction, pressure data may also be used to directly monitor cardiac activity separately from, or without, an EGM. An example of this is shown in FIG. 10. In this example, the mechanical rate is determined by the detection of right ventricular dP/dt crossing a threshold of 100 mmHg/s. Such embodiments may be useful in circumstances in which EGM data is not available or is not reliable, such as lead failure, lead fracture, undersensing or oversensing, and electromagnetic interference. For example, the IMD may detect a series of rapid pressure signals, determine that they are mechanical events and that this is a tachyarrhythmia, and may initiate an appropriate response.

In embodiments in which the IMD is a defibrillator, blanking of the mechanical activity may be appropriate following delivery of a defibrillating shock. Thus there may be a window, such as approximately 160 milliseconds, during which no mechanical event recordings are obtained or recorded. This may avoid a source of artifact in the mechanical event data.

The invention claimed is:

1. A method of confirming that an EGM deflection represents an R-wave comprising:
   sensing an EGM via an implantable medical device (IMD);
   sensing an intracardiac pressure via the IMD;
   determining a dP/dt of the sensed intracardiac pressure;
   detecting an electrical event using the EGM;
   opening a time window after detecting the electrical event;
   determining a maximum positive dP/dt of the intracardiac pressure sensed during the open time window;
   detecting the presence of a mechanical event responsive to the maximum positive dP/dt being greater than a first threshold; and
   determining that the electrical event includes an R-wave responsive to the presence of the mechanical event;
   determining a minimum negative dP/dt of the intracardiac pressure sensed during the open time window; and
   detecting the presence of an oversensed T-wave or noise using the minimum negative dP/dt, the oversensed T-wave or noise being deemed present when the mechanical event is deemed absent and an absolute value of the minimum negative dP/dt is greater than a second threshold.

2. A method according to claim 1, further comprising withholding defibrillation when the EGM indicates a tachyarrhythmia and the oversensed T-wave or noise is deemed present.

3. A method according to claim 1, further comprising detecting the presence of an R-wave with no corresponding mechanical event, the R-wave without a corresponding mechanical event being deemed present when the mechanical event is deemed absent and an absolute value of the minimum dP/dt is not greater than a second threshold.

4. A method according to claim 1, further comprising recording the presence of the mechanical event by the device on a marker channel.

5. A method according to claim 1, wherein the first threshold is approximately 100 mmHg/s.

6. A method according to claim 1, wherein the time window is between approximately 400 and approximately 500 milliseconds or equal to the duration between two sequentially detected R-waves, which ever is smallest.

* * * * *